United States Patent [19]

Zhang et al.

[11] Patent Number: 5,144,554
[45] Date of Patent: Sep. 1, 1992

[54] APPARATUS FOR DIAGNOSING AND PROVIDING THERAPY FOR GASTROINTESTINAL DISEASES WITHOUT CAUSING PATIENT DISCOMFORT AND INJURY

[76] Inventors: Xueshan Zhang; Lin Zhou, both of No. 2 Huashanxiang, Wuchenglu, Kunming City, Rep. of Korea

[21] Appl. No.: 487,265

[22] Filed: Mar. 2, 1990

[30] Foreign Application Priority Data

Mar. 4, 1989 [KR] Rep. of Korea .................. 89202531

[51] Int. Cl.$^5$ ............................................. G06F 15/42
[52] U.S. Cl. ................................ 364/413.02; 128/907
[58] Field of Search .................. 128/907, 630, 653.2; 364/413.02

[56] References Cited

U.S. PATENT DOCUMENTS

| | | | |
|---|---|---|---|
| 3,064,641 | 11/1962 | Manenti et al. | 128/907 |
| 4,556,064 | 12/1985 | Pomeranz et al. | 128/907 |
| 4,603,703 | 8/1986 | McGill et al. | 128/733 |
| 4,644,959 | 2/1987 | Calmanovici | 128/733 |
| 4,779,199 | 10/1988 | Yoneda et al. | 128/630 |

FOREIGN PATENT DOCUMENTS

| | | |
|---|---|---|
| 0257989 | 3/1988 | European Pat. Off. |
| 0269796 | 6/1988 | European Pat. Off. |
| 0940377 | 8/1983 | U.S.S.R. |
| 1316687 | 6/1987 | U.S.S.R. |

*Primary Examiner*—Gail O. Hayes
*Attorney, Agent, or Firm*—Hill, Van Santen, Steadman & Simpson

[57] ABSTRACT

A diagnostic and therapeutic apparatus for gastrointestinal diseases which has a central control unit a set of diagnosis and therapy lead electrodes, diagnosis and therapy switch, acupunctural point stimulating pulse amplifier, display, and a human body spectrum generator. During the diagnostic operation, bioelectric signals from a patient stomach received by the lead electrodes are supplied to the central control unit via the switch and displayed on a display. During the therapeutic operation, the human body spectrum generator radiates a simulated human body spectrum which matches with the spectrum of the human stomach to reinstate the abnormal spectrum of the patient so that gastrointestinal diseases can be cured. Meanwhile, the acupunctural point stimulating pulse amplifier introduces point stimulating pulses to the relevant accupoints of the patient body via the switch and lead electrodes for therapeutic purpose.

15 Claims, 6 Drawing Sheets

APPARATUS FOR DIAGNOSING AND PROVIDING THERAPY FOR GASTROINTESTINAL DISEASES WITHOUT CAUSING PATIENT DISCOMFORT AND INJURY

The present invention relates to a diagnostic and therapeutic apparatus, particularly to diagnostic and therapeutic apparatus for gastrointestinal diseases.

BACKGROUND OF THE INVENTION

The most frequently used methods in clinic for diagnosing gastrointestinal diseases such as gastric ulcers and duodenal ulcer at present include X-ray diagnosis, barium meal examination, gastroscopy and gastric juice analysis. These complicated examination procedures which are mostly carried out directly or indirectly within a patient's body may bring discomfort or even injury to the patient, and can not be used to diagnose functional disorder of gastrointestinal tract.

Until now, the effective treatment for gastrointestinal diseases is pharmacotherapy in which cimetidine, WEISENU, doxepin are usually used for gastrelcoma, and colloial dismutk sudcitrate is used for erosive doudemis. The curative effect of these drugs is low while the course of treatment is relatively long (usually several months) and accompanied with some side effects which can not be neglected.

SUMMARY OF THE INVENTION

The object of present invention is to provide a diagnostic and therapeutic apparatus which can diagnose gastronintestinal diseases such as gastric ulcer and duodenal ulcer and even the functional disorders of gastrointestinal tract which can not be diagnosed by conventional examinations and a manner such that no disconfort and injury to the patient will be caused by the diagnostic method of the present invention and the diagnosis can be carried out conveniently and reliably, and the therapy according to the diagnosis can be carried out without the side effects of pharmacotherapy. The diagnosis and therapy can be preferably coordinated by the present invention and the whole process (diagnosis and therapy) is quick and effective with no accompanied side effects of pharmacotherapy.

Experiments show that the bioelectric signal produced by rhythmic motility of the normal human stomach is of a frequency of 1/20 Hz (cycle: 20 sec.), and a amplitude of 150-250 uV. A deviation from the normal rhythmic motility (whether a positive one or a negtive one) indicates that certain pathologic changes exist in the gastrointestinal tract. Therefore, gastrointestinal diseases can be diagnosed by detecting the changes of the bioelectric signals of the motility of the human stomach.

The inventors of this invention have discovered that irradiating a simulated human body spectrum which matches the normal human stomach spectrum and with an energy which is much higher than that of the normal human stomach spectrum to the human stomach will resonate the human stomach spectrum and thus recover the abnormal human spectrum to normal relationship so that gastrointestinal diseases can be cured. Besides, according to the theory of traditional Chinese medicine, stimulating the human stomach and intestine or the acupoint Tsusanli may cure gastrointestinal diseases.

On these grounds, to achieve the object of the present invention, the diagnostic and therapeutic apparatus for gastrointestinal disease according to the present invention comprises:

power supply means;

a central control unit consisting of a single chip computer and peripheral devices;

a keyboard;

a set of diagnosis and therapy lead electrodes;

diagnosis and therapy switching means having a first input, a second input, and an output and an input/output said first input being connected to said central control unit, said input and output being connected to said set of diagnosis and therapy lead electrodes; a kymograph with its input connected to said output of said switching means, and its output supplied to said central control unit via an A/D converter;

an acupoint stimulating pulse amplifier with its input connected to said central control unit and its output coupled to said second input of said switching means;

a first display connected to said central control unit;

a human body spectrum generator;

an adjustable electronic switch having an input, first and second outputs, said input being connected to said central control unit, said first output being coupled to said human body spectrum generator and;

an electronic timer connected to said central control unit.

BRIEF DESCRIPTION OF THE DRAWINGS

In the drawings, like parts will be indicated by like numerals.

DETAILED DESCRIPTION OF THE PREFERRED EMBODIMENT

Figure 1:
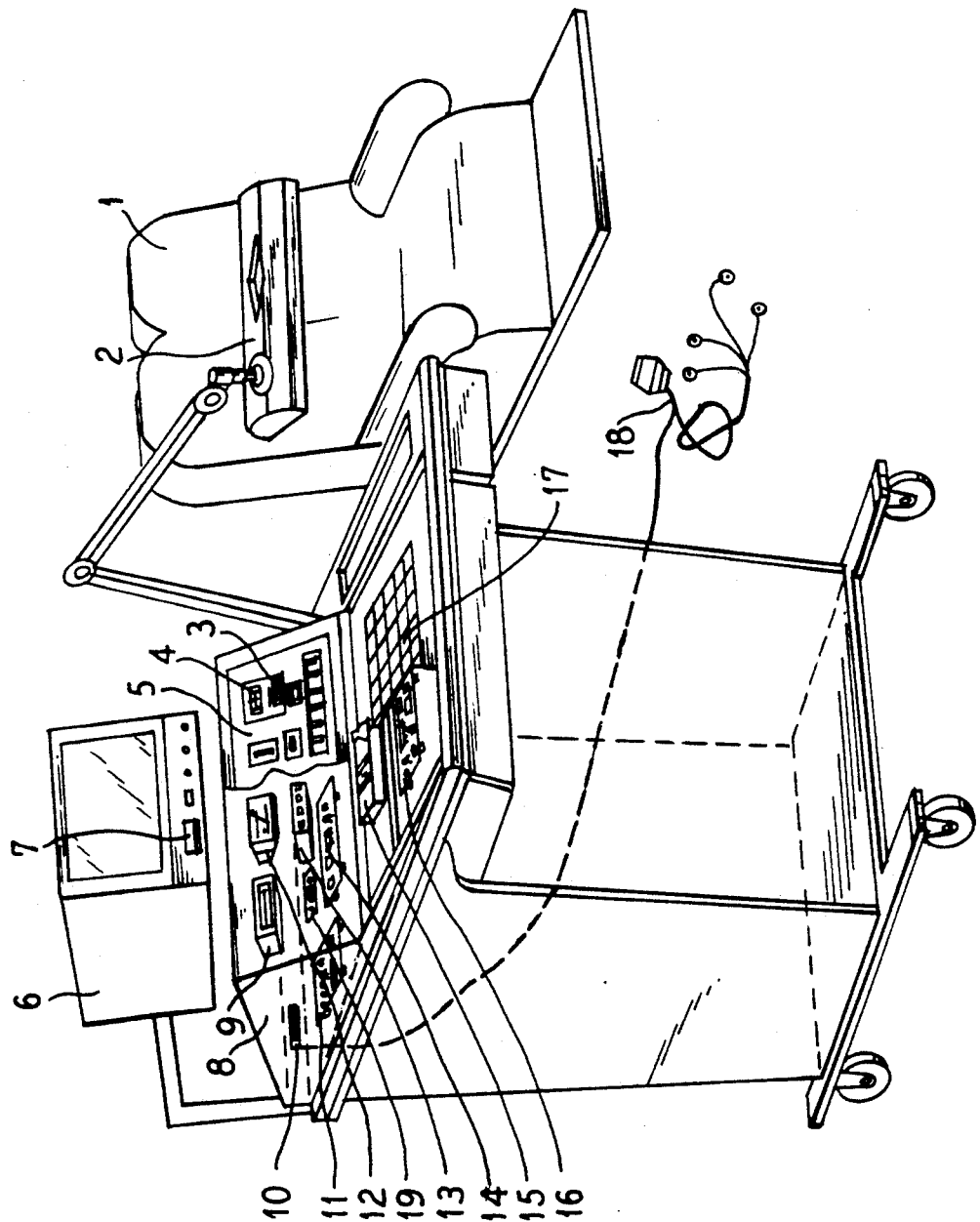
FIG. 1 schematically shows the structure of an apparatus according to the present invention.

FIG. 1 shows the structure of an apparatus according to the present invention. In FIG. 1, numeral 2 represents a therapeutic probe carrying a human body spectrum generator, which is coupled by an universal coupling. An adjustable electronic switch 3 is used to control the therapeutic dose of probe 2. A field intensity monitor 4 displays the therapeutic dose of probe 2. A cathode ray tube (CRT) 6 displays the patient's condition, 6 and diagnosis, as well as the frequency and amplitude of the acupoint stimulating pulse. A printer 7 may print out the whole process of the diagnosis and therapy step by step. A music means 9 is used to relax the nervous system of the patient to avoid deviations of the bioelectric signal of from the normal waveform caused by the patient's behavior such as swallowing saliva under nervous tension. An electronic timer 13 is used to control the therapeutic period; and numeral 19 represents a language processor constituted by a special integrated circuit such as UM 5101 for recording and reproducing certain introductive explanation.

Figure 2A:
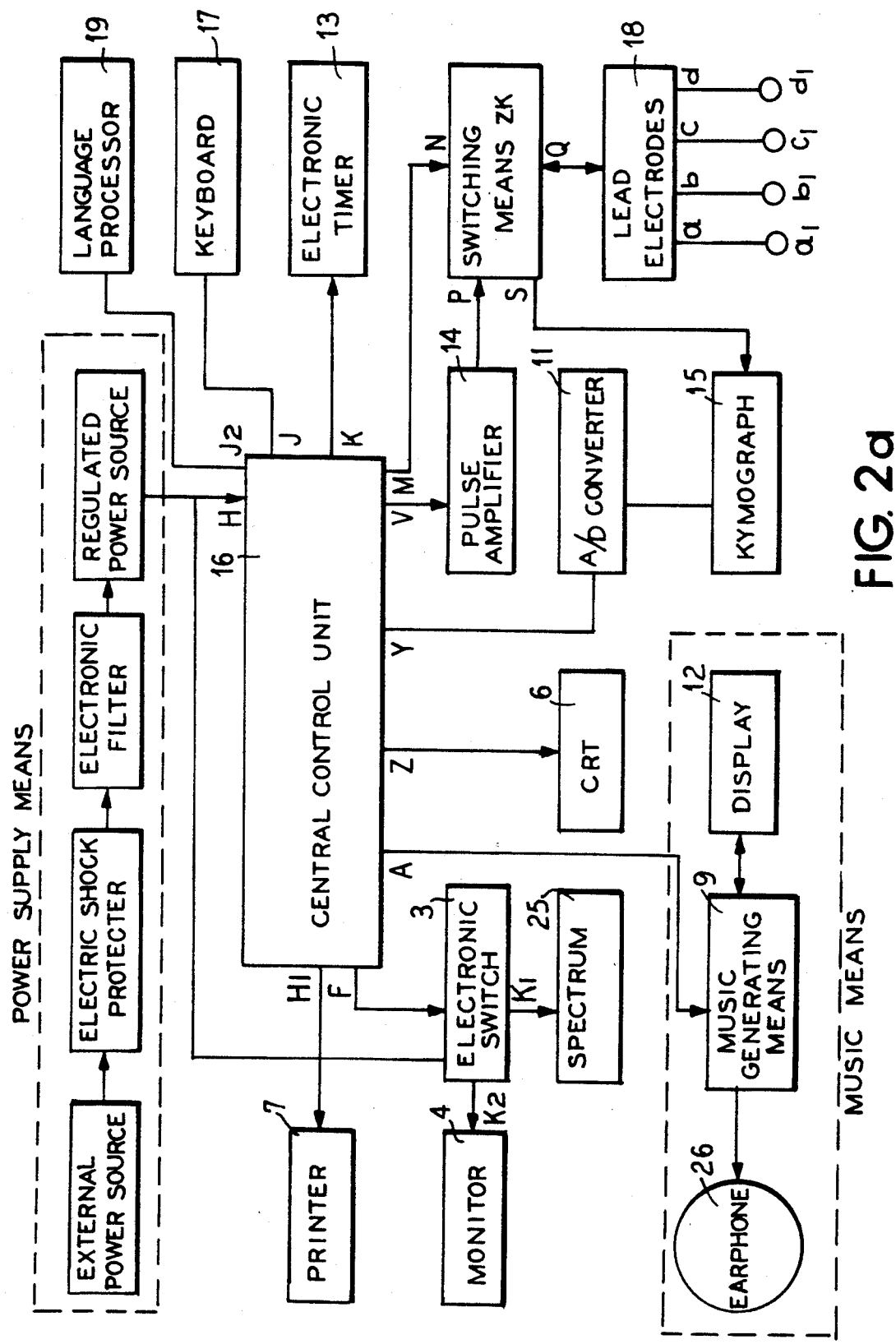
FIG. 2a is the circuit arrangement of an embodiment according to the present invention.

FIG. 2a is the circuit arrangement of an embodiment according the present invention. Power supply means for powering the whole system comprises an external power source, an electric shock protector, a filter for filtering possible high frequency interference to the central control unit 16 and kymograph 15, and a regulated power supply to insure the reliable operation of the whole system.

Central control unit 16 consisting of a single chip computer such as types 8751, 8039 and 8096, and peripheral devices PIO, STC and CTC has 11 external interfaces: H, J J2, K, M, V, Y, Z, A, F and H1. H is the power supply input. Those skilled in the art may adopt any commericially available single chip computer and peripheral devices for the central control unit and therefore the detailed description of the central control unit is omitted for simplicity. In the ROM of the central control unit 16, typical cases of gastrointestinal diseases are stored. The waveforms of bioelectrical signals produced by the rhythmic gastrointestinal motility EGGs (Electro Gastric Graph) of patients with various gastrointestinal diseases are obtained by applying a set of lead electrodes on the acupoints of the body surface (FIG. 6). The characteristics of different EGGs are associated with various gastrointestinal diseases which are classified by the conventional gastroscopy. The characteristics of the EGGs of some typical cases of gastrointestinal diseases are shown in FIGS. 1-9.

These typical EGGS are obtained similar to obtaining EGGs (Electro Cardiac Graphs). The bioelectric signals of EGG are much weaker than those of EGG (micro-volt) range vs. milli-volt range). The bioelectric signals of EGGs are converted to digital signals by A/D converter 11 for storage on a disk.

Keyboard 17 is the input port for "operator-computer interaction". The operator may control the apparatus to perform various functions by inputting corresponding commands for diagnositic or therapeutic purposes. Keyboard 17 is connected to interface J of central control unit 16.

The set of diagnosis and therapy lead electrodes 18 are same as the set of the lead electrodes for EGG and are commercially available. By a diagnosis and therapy switching means ZK, the set of the lead electrodes 18 are used both to transmit the bioelectric signals of the gastrointestinal motility for diagnosis and to transmit acupoint stimulating pulses and/or the simulated human body spectrum to the relevant acupoints on the body surface for therapy. The lead electrodes 18 are conventional body surface like electrodes which produce no pain or injury to the patient for diagnosis and therapy. The set of lead electrodes are connected to input/output Q of a diagnosis and therapy switching means ZK. Diagnosis and therapy switching means ZK is controlled by the central control unit 16 so as to switch between diagnosis and therapy in accordance with the command input from keyboard 17. Switching means Zk may be composed of an analogue switch type CD 4051 or similar elements. A first input N of the switching means ZK is connected to interface M of the central control unit 16, while the output thereof is coupled to Kymograph 15. Kymograph 15 records the bioelectric signals picked up by the lead electrodes 18 during diagnostic process. It can be any type of commercially available kymograph. The output of kymograph 15 is supplied to the central control unit 16 via an A/D converter 11 at interface Y. The bioelectric signals are converted to digital signals by A/D converter 11 and are displayed on cathode ray tube (CRT) 6. Meanwhile, the digitized signals are compared with the cases stored in the ROM and a diagnosis is made accordingly. The diagnosis is then displayed on CRT 6. Acupoint stimulating pulse amplifier 14 performs power amplification of the acupoint stimulating pulses generated by the computer in accordance with the command from keyboard 17. The frequency and amplitude of these pulses simultaneously are displayed on CRT 6.

The square waves or dilatational waves of the acupoint stimulating pulses are appropriate to treat gastrointestinal diseases since these waves are similar to those of EGG for normal healthy persons. The acupoint stimulating pulses are applied to the relevant acupoints on human body via switching means ZK and the lead electrodes 18. One skilled in the art would know the most relevant acupoints (FIG. 8) for the gastrointestine which have been well established in Tradional Chinese Medicine for initiation of pulses into the body to treat gastrointestinal diseases. Its therapeutic dose is controlled by central control unit 16 through an adjustable electronic switch 3. The adjustable electronic switch 3 is an automatic and manual switch. Its input is connected to the central control unit 16. A second output of switch 3 is applied to a field intensity monitor 4 which displays the therapeutic dose of the human body spectrum generator 25. An electronic timer 13 is connected to the central control unit 16 at interface K and controls the therapeutic duration of the apparatus. It can be any commercially available electronic timer having timing, display and alarm functions. By the end of the therapeutic duration, timer 13 may request the computer to cut off power supply to the human body spectrum generator 25.

Figure 2B:
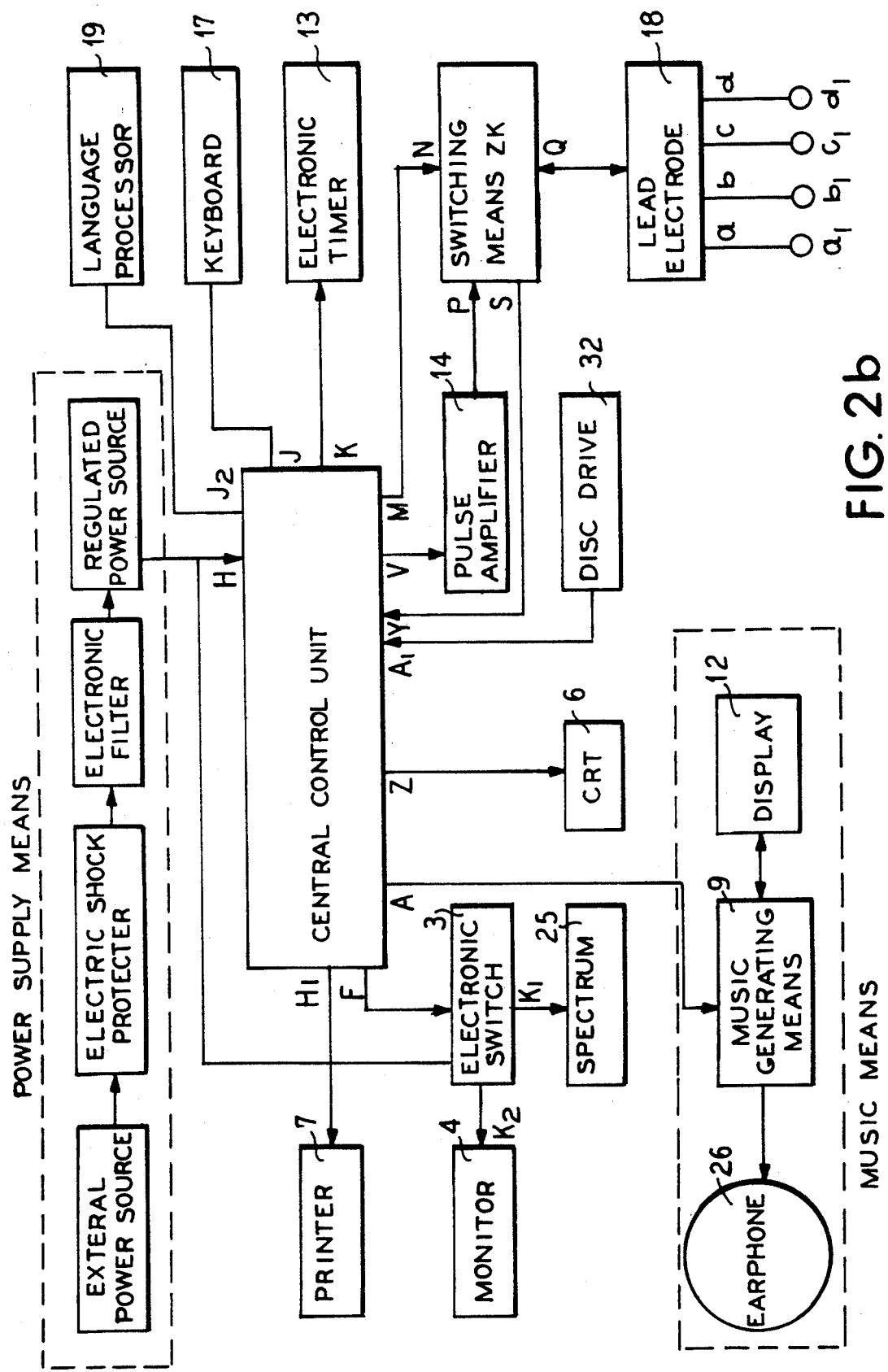
FIG. 2b is the circuit arrangement of another embodiment according to the present invention.

FIG. 2b is the circuit arrangement of another embodiment according to the present invention. The descriptions of the same parts as in FIG. 2a are omitted for simplicity. Central control unit 16 is consituted by a personal computer instead of a single chip computer and peripheral devices PIO, AD/DA board, print board, display board, bioamplifier etc. In addition to the interfaces shown in FIG. 2a, the FIG. 2a embodiment has an extra one, A1 for disc drive, thus the capacity of central control unit 16 can be expanded. The A/D converter in FIG. 2a is replaced by an AD/Da board within the central control unit 16. The bioelectric signals which are picked up by the lead electrodes 18 are applied to the central control unit 16 directly without being recorded by a kymograph so that the operator can monitor the patient's conditions directly on CRT 6. The bioelectric signals of the patient's EGG before and after the therapy (the patient's conditions) can be converted to digital signals by A/D converter 11 for storage on a disk.

Figure 3:
FIG. 3 is the sectional view of the human body spectrum generator according to the present invention.
Figure 4:
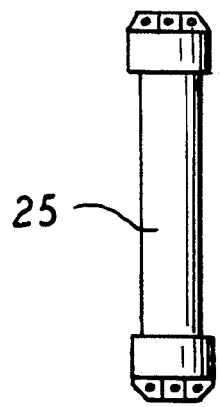
FIG. 4 shows the contour of the human body spectrum generator according to the present invention.

FIGS. 3 and 4 schematically show the human body spectrum generator 25. The inventors of this invention have discovered that an energy radiating material coated thereon with a mixed layer composed of certain oxides and metals can radiate a simulated human body spectrum which matches the human stomach spectrum. By irradating such a simulated human spectrum to the stomach and intestine can trigger resonance in the human body and thus reinstate the abnormal spectrum of the stomach so that gastrointestinal diseases can be cured. The human body spectrum generator according to the present invention is composed of three layers. The first layer is a substrate made of an insulating material such as borosilicate glass, porcelain, fireproof material or microcrystalline glass etc. The second layer is a semiconductor transducer. The third layer is a mixed layer (spectrum radiating layer). Experiment shows that the spectrum radiating layer is preferably composed of the following materials: boron oxide, silicon dioxide, magnesium oxide, ferric oxide, manganese oxide, molybdenum oxide, zinc oxide, lithium oxide, cupric oxide, titanium oxide, strontium oxide, chromic oxide, cobaltous oxide, vanadium oxide, chromium, aluminum oxide, arsenic oxide. calcium oxide, sodium oxide, and potassium oxide. The preferred mixing ratio is 12.5/78.8/0.3/1/0.1/0.1/1/0.1/0.1/ 0.1/0.1/2/0.2/0.1/0.05/0.5/0.1/0.1/3/0.1.

Human body spectrum generator 25 can also be manufactured using the teachings of Chinese Patent Application CN 87103603, i.e. mixing the above mentioned 20 materials in the above specified ratio with an insulating material such as borosilicate glass into an integral material at high temperature, and then forming a transducing layer on its inside surface. The output power of the generator should be higher than 20 watts and the surface area of the spectrum radiating layer should be larger than 4cm² no matter what structure is adopted. In addition to this, the generator may also be made by coating a spectrum radiating layer composed of above-mentioned 20 materials in the above-mentioned ratios on an infrared or a magnetic radiator whose wavelength coverage is 0.72-25 um, and the output power is higher than 20 Watts. However, the surface area of the spectrum radiating layer must be larger than 4cm².

Figure 5:
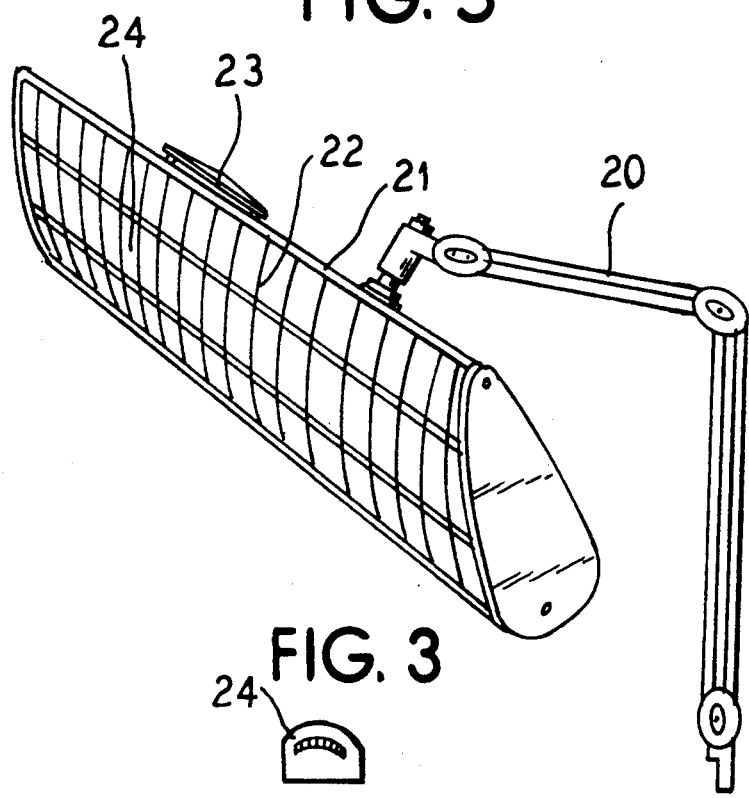
FIG. 5 schematically shows the therapeutic probe according to the present invention.
Figure 6:
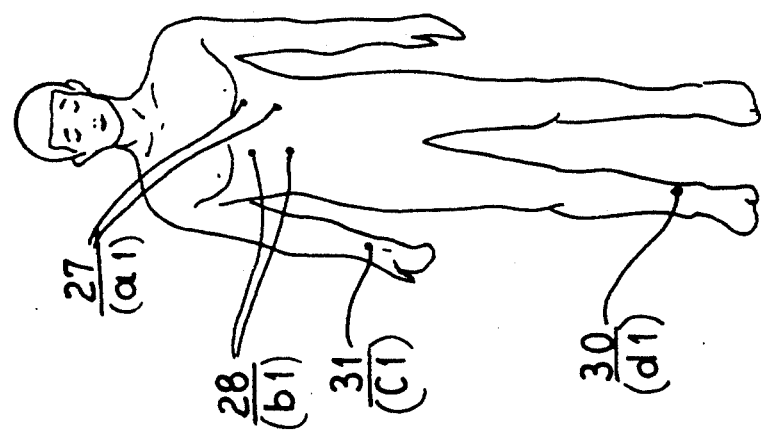
FIG. 6 schematically shows human body acupoints in relation to the diagnosis with the apparatus according to the present invention.

FIG. 5 is the therapeutic probe carrying a human body spectrum generator according to the present invention. Hollow arm 20 constitutes the connection between the human body spectrum gengerator 25 and the apparatus. Housing 21 holds generator 25. Protecting net 22 prevents the spectrum radiating layer from being damaged.

Figure 7:
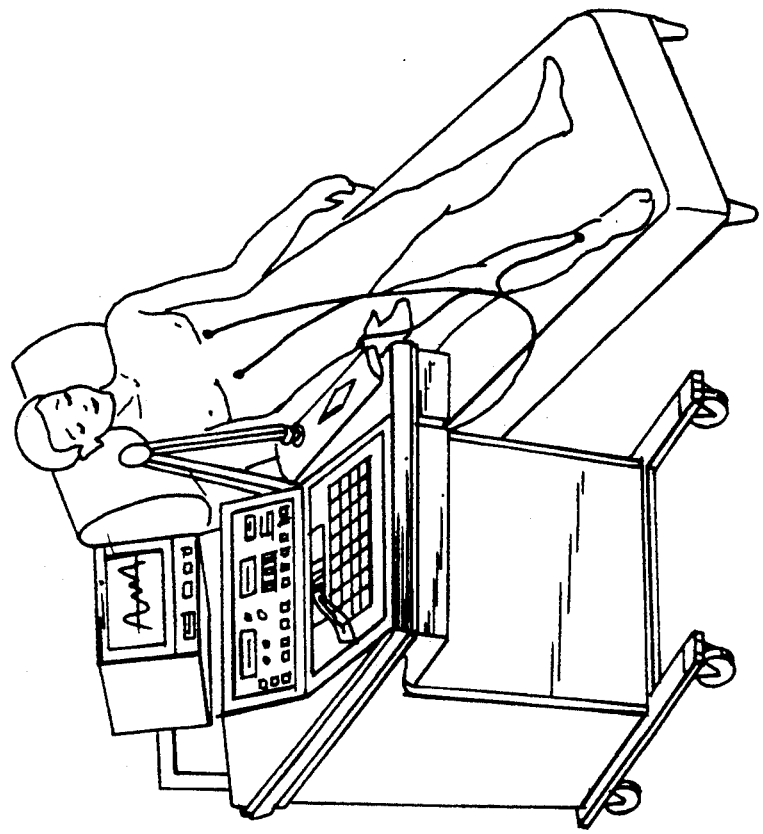
FIG. 7 schematically shows the diagnosis with the apparatus according to the presents invention.

FIG. 6 shows human body acupoints in relation to diagnosis with the apparatus according to the present invention. 27 indicates position of the stomach, 28 indicates the gastric antrum. Experiment shows that the bioelectric signals sampled from these two points best reflect the pathologic changes of the gastrointestinal tract. 30 indicates a grounding point while 31 indicates a reference point. During the diagnostic operation, lead electrodes 18 contact the relevant points in a manner similar to that during an electrocardiographic examination (as shown in FIG. 7) while diagnosis/therepy switching means ZK is switched to the diagnosis position. At this time, the channel for the acupoint stimulating pulses is blocked. The waveform of bioelectric signals received by electrodes 18 is displayed on CRT 6. A clinical trial of 400 cases shows that diagnosis with the apparatus according to the present invention coincides with that with conventional methods by 75%.

Figure 8:
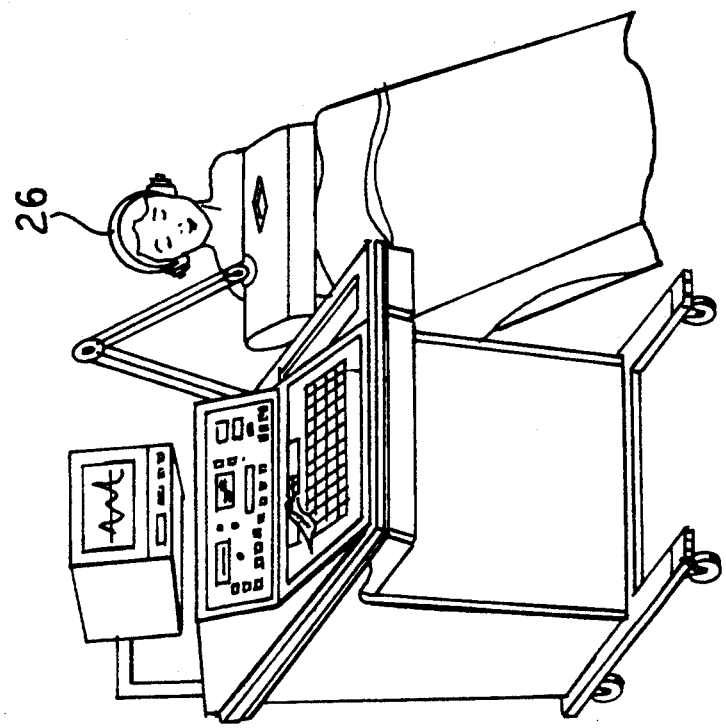
FIG. 8 schematically shows human body acupunctrual points in relation to the therapy with the apparatus according to the present invention.
Figure 9:
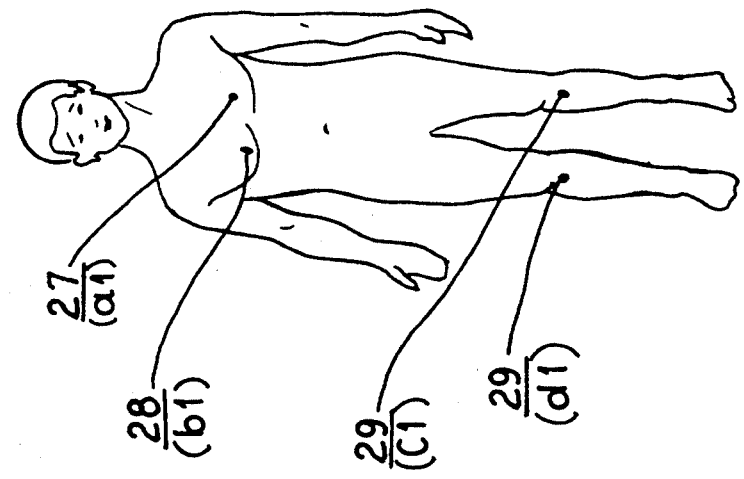
FIG. 9 schematically shows the therapy with the apparatus according to the present invention.

FIG. 8 shows the human body acupoints in relation to therapy. 27 and 28 indicate, respectively, the positions of the stomach and the gastric antrum. 29 indicates Tsusanli accupoint. During the therapeutic operation, the therapeutic probe 2 which carries the human body spectrum generator 25 is placed near the patient's body between the xiphoid process (not shown) and navel, i.e. body of stomach and gastric antrum. For colitis, probe 2 is placed near the patient's body at the lower abdomen. The appropriate therapeutic dose is the one that brings no discomfort to the patient. Meanwhile, the acupoint stimulating pulses can be introduced to Tsusanlis accupoints by contacting the lead electrodes 18 to these points for therapeutic purpose in view of the theory of traditional Chinese medicine that stimulating Tsusanli etc. would heal gastrointestinal disorders.

Tracing observation shows that symptoms such as abdominal distention, abdominal pain, sour regurgitation, eructation and anorexia etc. disappear after five (5) treatments (30 minutes each treatment). The cure rate gastric ulcer gastrelcoma and duodenal ulcer after four (4) weeks treatment (once a day, 30 minutes each time) is over 84.4% while the effective rate is over 96.6%, wherein, clinically confirmed effective rate after 10 treatments is over 80% and that after 20 treatments is over 90%.

Table 1 statistically reveals the therapeutic efficacy of the apparatus according to the present invention in the treatment of 112 cases of gastric ulcer and duodenal ulcer:

TABLE 1

| number of treatments | notably effective | effective | non effective | total | Percentage |
|---|---|---|---|---|---|
| 10 | 5 | 12 | 4 | 21 | 81 |
| 20 | 24 | 8 | 1 | 33 | 97 |
| 30 | 48 | 10 | 0 | 58 | 100 |
| Total | 77 | 30 | 5 | 112 | 92.7 |

It can be seen from table 1 that notably effective (77 cases) account for 68.80%, effective (30 cases) account for 26.7%, noneffective (5 cases) account for only 4.5%. The total effective rate is 95.5%.

The above description of the present invention is made for two particular embodiments. However, the present invention covers all modifications and amendments by those skilled in the art without departing from the spirit and scope of the present invention.

We claim:

1. A diagnostic and therapeutic apparatus for gastrointestinal diseases comprising:
   power supply means;
   a central control unit consisting of a single chip computer and peripheral devices:
   a keyboard;
   a set of diagnosis and therapy lead electrodes;
   diagnosis and therapy switching means having a first input, a second input, and output and a common input and output terminal, said first input being connected to said central control unit, said common input and output terminal being connected to said set of diagnosis and therapy lead electrodes;
   a kymograph with its input connected to said output of said switching means, and its output supplied to said central control unit via an A/D converter;
   an acupoint stimulating pulse amplifier with its input connected to said central control unit and its output coupled to said second input of said switching means;
   a first display means connected to said central control unit:
   a human body spectrum generator;

an adjustable electronic switch having an input, a first and a second output, said input being connected to said central control unit, said first output being coupled to said human body spectrum generator; and an electronic timer connected to said central control unit.

2. The apparatus according to claim 1, wherein said human body spectrum generator comprises a substrate, a transducing layer and a spectrum radiating layer.

3. The apparatus according to claim 2 wherein said spectrum radiating layer is composed of the following materials boron oxide, silicon oxide, magnesium oxide, ferric oxide, manganese oxide, molybdenum oxide, zinc oxide, lithium oxide, cupric oxide, titanium oxide, strontium oxide, chromic oxide, cobaltous oxide, vanadium oxide, chromium, aluminium oxide, arseric oxide, calcium oxide, sodium oxide, and potassium oxide; the preferred mixing proportion of said materials is 12.5/78.8/0.3/1/0.1/0.1/1/0.1/0.1/ 0.1/0.1/2/0.2/0.1/0.05/0.5/0.1/0.1/3/0.1 and the surface area of said spectrum radiating layer is at least 4cm$^2$.

4. The apparatus according to claim 1 further comprising a second display means connected to said second output of said adjustable electronic switch for displaying the therapeutic dose of said human body spectrum generator.

5. The apparatus according to claim 1 further comprising printing means connected to said central control unit.

6. The apparatus according to claim 1 further comprising music means for relaxing the nervous system of a patient.

7. The apparatus according to claim 1, wherein said adjustable electronic switch is an automatic and manual switch.

8. The apparatus according to claim 2, wherein said substrate and spectrum radiating layer are fabricated into an integral structure.

9. A diagnostic and therapeutic apparatus for gastrointestinal diseases such as gastrelcona, comprising:
   power supply means;
   a central control unit consisting of a personal computer and peripheral devices;
   a keyboard;
   a set of diagnosis and therapy lead electrodes;
   diagnosis and therapy switching means having a first input, a second input, an output and a common input and output terminal, said first input being connected to said central control unit, said common input and output terminal being connected to said set of lead electrodes, said output supplying signals sampled by said lead electrodes to said central control unit;
   an acupoint stimulating pulse amplifier with its input connected to said central control unit, and its output coupled to said second input of said switching means;
   a first display means connected to said central control unit;
   a human body spectrum generator;
   an adjustable electronic switch having an input and first and second outputs, said input being connected to said central control unit, said first output being coupled to said human body spectrum generator; and
   an electronic timer connected to said central control unit.

10. The apparatus according to claim 9 further comprising a second display means connected to said second output of said adjustable electronic switch.

11. The apparatus according to claim 9 further comprising music means.

12. The apparatus according to claim 9 further comprising printing means.

13. The apparatus according to claim 9, wherein said adjustable electronic switch is an automatic and manual switch.

14. The apparatus according to claim 9, wherein said human body spectrum generator comprises a spectrum radiating layer composed of the following materials: boron oxide, silican oxide, magnesium oxide, ferric oxide, manganese oxide, molybdenum oxide, zinc oxide, lithum oxide, cupric oxide, titanium oxide, strontium oxide, chromic oxide, cobaltous oxide, vanadium oxide, chromium, aluminium oxide, arsenic oxide, calcium oxide, sodium oxide, and potassium oxide; the preferred mixing proportion of said materials in said oridnal relation is 12.5/78.8/0.3/1/0.1/0.1/1/0.1/0.1/ 0.1/0.1/2/0.2/0.1/0.05/0.5/0.1/0.1/3/0.1; and the surface area of said spectrum radiating layer is at least 4cm$^2$.

15. The apparatus according to claim 9 further comprising a floppy disc drive.

* * * * *

UNITED STATES PATENT AND TRADEMARK OFFICE
CERTIFICATE OF CORRECTION

PATENT NO. : 5,144,554
DATED : September 1, 1992
INVENTOR(S) : Zhang et al

It is certified that error appears in the above-indentified patent and that said Letters Patent is hereby corrected as shown below:

On the title page, item [30] change "(KR) Rep. of Korea" to —(PRC) Peoples Rep. of China—.

Column 3, line 2, after "signal of" insert —the stomach— and continue with "from the normal", etc.

Column 6, line 16, change "The cure rate" to —The cure rate of—, line 17, delete "gastrelcoma".

Signed and Sealed this

Sixth Day of December, 1994

Attest:

BRUCE LEHMAN

Attesting Officer     Commissioner of Patents and Trademarks